United States Patent [19]

Laverick et al.

[11] 4,340,447
[45] Jul. 20, 1982

[54] PROCESS FOR THE RECOVERY OF PURE ACETONE FROM CUMENE HYDROPEROXIDE CLEAVAGE REACTION PRODUCT

[75] Inventors: Robert G. Laverick, Sandy, England; James M. Scotland, Stirlingshire, Scotland

[73] Assignee: BP Chemicals Limited, London, England

[21] Appl. No.: 267,603

[22] Filed: May 27, 1981

[30] Foreign Application Priority Data

May 27, 1980 [GB] United Kingdom ................. 8017367

[51] Int. Cl.$^3$ .................... B01D 3/34; C07C 49/08
[52] U.S. Cl. ................................. 203/36; 203/37; 203/38; 203/74; 203/87; 203/DIG. 19
[58] Field of Search ..................... 203/33, 36, 37, 38, 203/74, 71, 87, 99, DIG. 19; 568/385, 410, 411

[56] References Cited

U.S. PATENT DOCUMENTS

| | | | |
|---|---|---|---|
| 2,737,480 | 3/1956 | Adams et al. | 203/33 |
| 3,265,592 | 8/1966 | Van Der Weel | 568/410 |
| 3,330,741 | 7/1967 | Theilig et al. | 203/37 |
| 3,531,376 | 9/1970 | Minoda et al. | 203/37 |
| 3,547,783 | 12/1970 | Yamaguchi et al. | 203/37 |
| 3,668,256 | 6/1972 | Brundege | 568/411 |
| 3,672,961 | 6/1972 | Nixon | 568/492 |

Primary Examiner—Wilbur L. Bascomb, Jr.
Attorney, Agent, or Firm—Brooks, Haidt, Haffner & Delahunty

[57] ABSTRACT

Pure acetone is recovered from a crude acetone vapor fraction removed overhead from a first column separating phenol and higher boilers as a bottom fraction from a cumene hydroperoxide cleavage reaction product by partially condensing the crude acetone fraction, returning the condensed portion of the crude acetone fraction to the first column as reflux, feeding the remaining portion as a vapor to an intermediate point in a second distillation column to which there is also fed continuously at a point above the acetone feedpoint a dilute aqueous solution of an alkali, removing from the base of the second column a residue fraction comprising compounds boiling above acetone, removing from a point in the second column intermediate between the alkali feedpoint and the top of the column as a liquid sidedraw fraction pure acetone having a permanganate time (PT) greater than 4 hours, and removing from the top of the second column as a vapor fraction acetone having a PT less than that of the sidedraw fraction, condensing the acetone vapor fraction and returning to the second column at a point above the liquid acetone sidedraw removal point a portion of the condensate as reflux.

10 Claims, 1 Drawing Figure

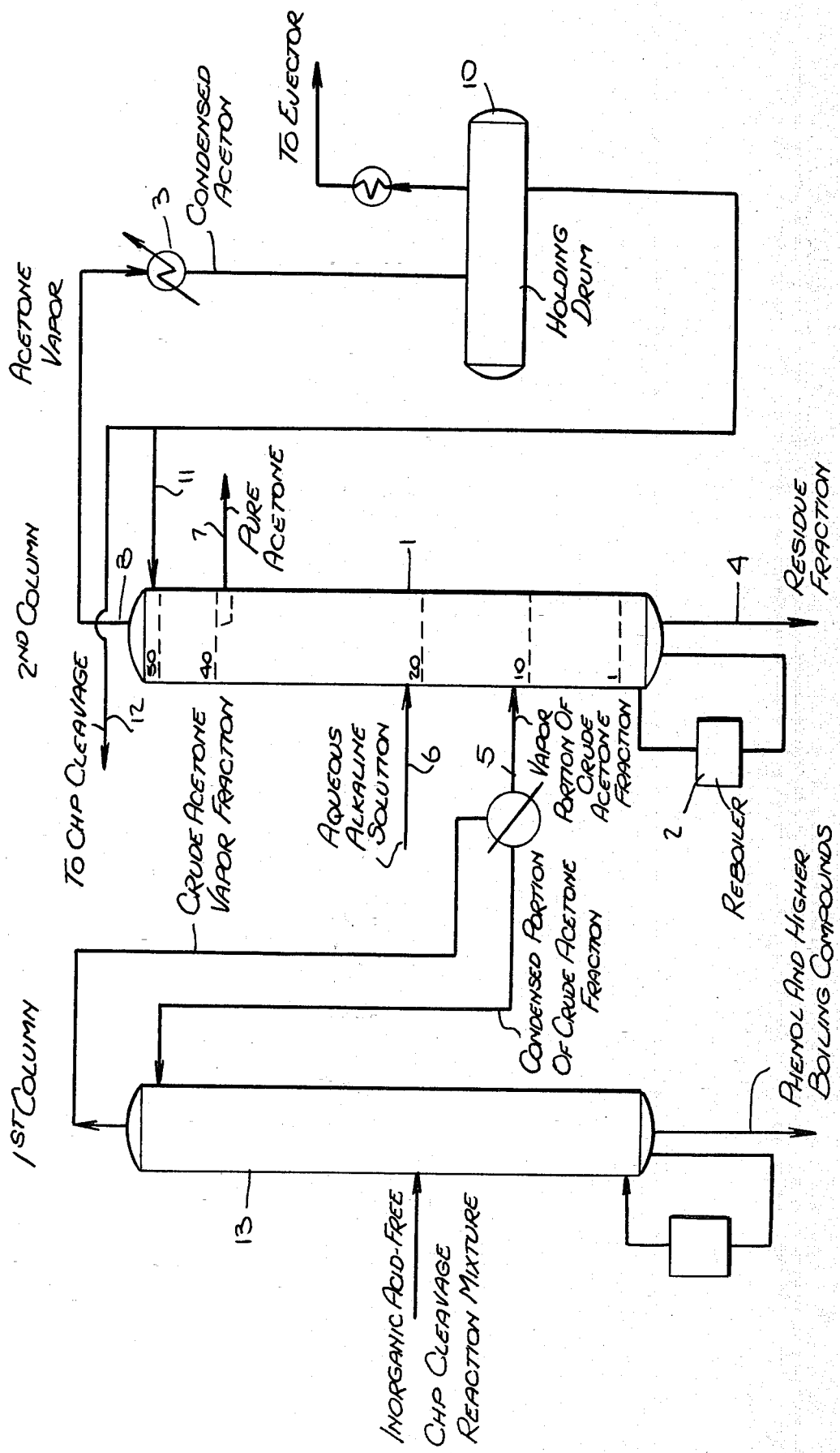

PROCESS FOR THE RECOVERY OF PURE ACETONE FROM CUMENE HYDROPEROXIDE CLEAVAGE REACTION PRODUCT

The present invention is directed to the process for the production of phenol and acetone by cleavage of cumene hydroperoxide and in particular to a process for the recovery of pure acetone from the crude acetone obtained from the fractional distillation of cumene hydroperoxide cleavage reaction product.

The cleavage of cumene hydroperoxide produces phenol and acetone and varying amounts of sideproducts such as aldehydes, methanol, mesityl oxide, hydroxyacetone, alphamethylstyrene, acetophenone, cumyl phenols, phenyldimethyl carbinol ("carbinol"), organic acids, other higher phenols and high-boilers. In one process the cleavage products together with water and any unreacted cumene, which throughout this specification are referred to as the cumene hydroperoxide cleavage reaction product, after removal of any cleavage catalyst which may be present, is fed to a distillation column, hereinafter referred to as the crude acetone column, wherein there is removed overhead a crude acetone fraction containing material present in the feed with a boiling point lower than that of phenol and there is taken from the bottom of the column a fraction containing phenol, carbinol, acetophenone, cumyl phenols, higher phenols and high-boilers from which phenol is recovered in a series of fractional distillations. The crude acetone fraction removed overhead is condensed and part of the condensate is returned to the column as reflux. The crude acetone constituting the remainder of the condensate is not sufficiently pure to meet the requirements of British Standard Specification BS 509:1971 or to meet a typical commercial grade which is as follows:

| Purity | % mass min. | 99.5. |
|---|---|---|
| Relative density at 15.5°/15.5° C. | | 0.796–0.798 |
| Relative density at 20°/20° C. | | 0.791–0.793 |
| Relative density at 25°/25° C. | | 0.786–0.788 |
| Distillation range at 1.013 bar | | |
| initial boiling point | °C. | 55.7 |
| dry point | °C. | 56.7 |
| water content | % mass max. | 0.5 |
| acidity as acetic acid | % mass max. | 0.002 |
| Alkalinity | | Complies with BS limit test |
| Alcoholic impurities | | |
| Residue on evaporation | % mass max. | 0.001 |
| Colour | Hazen units max | 10 |
| Permanganate time | hours | 2½ |

The tests relating to the specification are carried out in accordance with the methods described in British Standard Specification BS 509:1971

In particular the crude acetone does not meet the specification for permanganate time which requires that the colour of potassium permanganate added to the acetone be retained for at least 2½ hours. Accordingly the crude acetone is further purified by a combination of chemical treatment and distillation. The nature and extent of the impurities present in the crude acetone fraction depend to some extent on the manner in which the process is operated. Relevant factors include for example the conditions under which the cumene hydroperoxide is cleaved and the mode of operating the crude acetone column. Impurities believed to be responsible for failure of the crude acetone to meet the specification for permanganate time are aldehydes such as acetaldehyde and propionaldehyde, and also mesityl oxide. The crude acetone normally also contains water to a greater or lesser extent hydrocarbons such as cumene and alphamethylstyrene, traces of organic acids such as formic and acetic acids and less than about 3% w/w phenol. Other impurities which may be present in the crude acetone and may contribute to its failure to meet the specification are methanol and hydroxyacetone.

One method of purifying the crude acetone is described in British Pat. No. 800,763 (The Distillers Company). In this method the substantially phenol-free crude acetone is distilled in a fractional distillation column in the presence of an aqueous solution of an alkali metal hydroxide, and pure acetone is removed as the overhead stream from the column. The aqueous solution of alkali metal hydroxide, which may be of concentration in the range about 1% to about 25% w/v, is fed to the column either above, below or at the same point as the acetone feed. In practice, and indeed in the examples illustrating the invention it is found necessary to operate the fractional distillation column in conjunction with a prior aldehyde stripping column in order to obtain acetone of sufficient purity to meet the more stringent demands imposed by current commercial usage.

We have now found that the heat inherent in the crude acetone vapour removed overhead from the column separating phenol and higher-boiling compounds as a bottom fraction from the cumene hydroperoxide cleavage reaction product can be utilised to fractionate the impurities present in the vapour in a single further distillation column from which pure acetone is removed as a liquid sidedraw fraction, with a consequent saving in heat energy and equipment costs. Moreover the economic saving can be achieved without incurring a loss in acetone purity.

Accordingly, the present invention provides a process for the recovery of pure acetone from a crude acetone fraction removed overhead as a vapour from a first column separating phenol and higher-boiling compounds as a bottom fraction from the cumene hydroperoxide cleavage reaction product which process comprises partially condensing the crude acetone fraction, returning the condensed portion of the crude acetone fraction to the first column as reflux, feeding the remaining portion of the crude acetone fraction whilst still in the vapour phase to an intermediate point in a second distillation column to which there is also continuously fed at a point above the acetone feedpoint a dilute aqueous solution of an alkaline material, removing from the base of the second column a residue fraction comprising compounds boiling above acetone, removing from a point in the second column intermediate between the alkaline material feed point and the top of the column as a liquid sidedraw fraction pure acetone having a permanganate time greater than 4 hours, and removing from the top of the second column as a vapour fraction acetone having a permanganate time less than that of the sidedraw-fraction, condensing the acetone vapour fraction and returning to the second column at a point above the liquid acetone sidedraw removal point a portion of the condensate as reflux.

The alkaline material may suitably be an alkali or alkaline earth metal oxide, hydroxide or phenate, of which the alkali metal hydroxide is preferred. Preferably the alkali metal hydroxide is sodium hydroxide. The rate at which the alkaline material is fed to the second column is suitably such that the concentration of the alkaline material in the residue fraction removed from the base of the column is in the range 0.01 to 5.0, preferably 0.2 to 0.4% w/w.

The second column is preferably operated at a reduced pressure in the range 0.3 to 0.8, preferably in the range 0.5 to 0.7 bar absolute at the top of the column.

The residue fraction removed from the base of the second column will invariably contain a minor proportion of the acetone fed to the column in addition to compounds boiling above acetone. For the purpose of minimising the concentration of acetone in the residue fraction it is preferred to provide the column with a reboiler. Suitably the reboiler may be maintained at a temperature in the range 80 to 120, preferably in the range 85° to 100° C., which temperatures pertain to a pressure of 0.6 bar at the column top. For other pressures at the column top the temperature ranges should be adjusted appropriately.

After condensing the vapour fraction removed from the top of the second column it is preferred to recycle to another part of the phenol from cumene process that part of the condensate not returned to the column as reflux.

The reflux to side draw ratio in the second column may suitably be in the range 4:1 to 25:1, depending upon the proportion of condensate from the second column which is recycled to another part of the phenol from cumene process.

The invention may be better understood by reference to the FIGURE which is a simplified schematic flow diagram showing a preferred arrangement of equipment useful in the performance of the process of the invention.

Referring to the FIGURE, 1 is a single distillation column containing 55 plates or trays operating under reduced pressure, only plates 1, 10, 20, 45 and 55 being illustrated for reason of simplicity. The column is provided with a conventional reboiler 2 connected to a source of heat, a condenser 3 for condensing the vapours leaving the column, outlet 4 for withdrawing a residue fraction from the base of the column, crude acetone fraction vapour feed inlet 5, aqueous alkaline solution inlet 6, purified acetone outlet 7, pipe 8 for conveying vapour removed overhead to the condenser 3, pipe 9 for conveying the condensed vapour to a holding drum 10, pipe 11 for returning part of the condensate as reflux to the column and pipe 12 for recycling the remainder of the condensate.

A crude acetone fraction comprising acetone, hydrocarbon, water, aldehydes, mesityl oxide, methanol, hydroxyacetone and less than 1% w/w phenol, obtained as a vapour fraction by partial condensation of the vapour fraction removed from the top of a column 13 in which a phenol-containing fraction is separated and removed as a base fraction from the catalyst-free cumene hydroperoxide cleavage reaction product, is continuously fed through inlet 5 which is located about 10 trays above the bottom of the column 1. Also continuously fed to column 1 through inlet 6, located about 20 plates above the bottom of the column, is a dilute aqueous solution of an alkali which mixes with the downflowing liquid in the column and serves to scrub the upflowing vapours. The dilute aqueous alkali removes aldehydes and any hydroxyacetone by promoting aldol condensation reactions thereby producing high-boilers.

The dilute aqueous alkali also removes any phenol present as sodium phenate and organic acids as their sodium salts. Removed from the base of column 1 through pipe 4 is a fraction composed mainly of compounds having a higher boiling point than acetone such as excess alkaline material, water, mesityl oxide, sodium phenate, sodium acetate, sodium formate and high-boiling impurities together with a small proportion of the acetone in the feed. The temperature of the reboiler 2 is maintained at such a value that the proportion of acetone in the residue fraction removed from the base of column 1 is minimised. Acetone of purity meeting the requirements of British Standard Specification BS 509:1971 and in particular having a permanganate time greater than 4 hours is removed through pipe 7 at a point about 45 trays above the base of the column as a liquid sidedraw fraction. Acetone having a lower permanganate time than the liquid sidedraw fraction by reason of its higher aldehyde content and containing also methanol but having a lower water content is removed from the top of column 1 through pipe 8 as a vapour fraction. The vapour fraction is condensed in the condenser 3 and passes through pipe 9 into tank 10. From tank 10 part of the condensate is returned through pipe 11 to the top of column 1 as reflux and the remaining portion of the condensate is recycled through pipe 12 to another point in the phenol from cumene process.

The purity of the liquid acetone sidedraw fraction can be improved beyond the requirements of BS 509:1971 to that demanded by present day commercial specifications for industrial acetone by selection of optimum process conditions.

The invention will now be illustrated by reference to the following Examples.

In the Examples the crude acetone vapour was obtained by feeding catalyst-free cumene hydroperoxide cleavage reaction product to a first distillation column wherein there is removed overhead a crude acetone vapour fraction containing material present in the feed with a boiling point lower than that of phenol and there is taken from the bottom of the column phenol and higher-boiling compounds. The crude acetone fraction removed overhead is partially condensed and the condensate is returned to the column as reflux. The remainder of the crude acetone fraction is used as the vapour feed in the Examples.

In all the Examples the plates are numbered upwards from the base of the column.

EXAMPLE 1

Crude acetone vapour containing impurities such as aldehydes (600 ppm), hydroxyacetone (4000 ppm), phenol (2800 ppm) and water was continuously fed to a 50 mm diameter 55 plate Oldershaw column fitted with a conventional reboiler maintained at 88° C. The pressure at the top of the column was 0.6 bar. The feed was introduced on tray 10 at a rate of 875 ml.h$^{-1}$ and a 1% w/w aqueous sodium hydroxide solution was fed to plate 20 at a rate of 300 ml h$^{-1}$. Liquid acetone satisfying the purity requirements of British Standard Specification BS 509:1971 and in particular having a permanganate time (PMT) in excess of 4 hours was removed as a sidedraw from plate 45. Impure acetone having a PMT lower than that of the sidedraw acetone was removed as an overhead distillate, condensed and part of the condensate was returned as reflux to the top of the column. The reflux ratio (reflux to sidedraw) was 4.6:1. Water, excess alkali, sodium phenate, sodium acetate, sodium formate, high-boiling materials and a little acetone were removed as a residue fraction from the base.

EXAMPLE 2

The procedure of Example 1 was repeated except that an equivalent weight of 2% sodium hydroxide was added to plate 20. The liquid acetone removed as a sidedraw conformed to BS 509:1971 and in particular had a PMT in excess of 4 hours.

EXAMPLE 3

Crude acetone vapour containing aldehydes (700 ppm), hydroxyacetone (3700 ppm) and phenol (1300 ppm) was continuously fed to a 50 mm diameter 55 plate Oldershaw column fitted with a conventional reboiler maintained at 95° C. The pressure at the column top was 0.6 bar. The feed was introduced on tray 10 at a rate of 1280 ml h$^{-1}$ and a 15% w/w aqueous sodium hydroxide solution was fed to plate 20 at 25 ml h$^{-1}$. The reflux to sidedraw ratio was 5.8:1. Fractions were removed from the column at the same points as in Example 1. The purity of the liquid acetone sidedraw was such that it conformed with BS 509:1971 and in particular the PMT was greater than 4 hours. The PMT of the acetone distillate removed overhead was less than that of the sidedraw.

EXAMPLE 4

Crude acetone vapour containing aldehydes (300 ppm) and hydroxyacetone (200 ppm) was continuously fed to a 50 mm diameter 55 plate Oldershaw column fitted with a conventional reboiler maintained at 94° C. The pressure at the column top was 0.6 bar. The feed was introduced on tray 10 at a rate of 880 ml h$^{-1}$ and a 15% w/w aqueous sodium hydroxide solution was fed to plate 20 at 15 ml h$^{-1}$. The reflux to sidedraw ratio was 6:1. Fractions were removed from the column at the same points as in Example 1. The purity of the liquid acetone sidedraw was such that it conformed with BS 509:1971 and in particular the PMT was greater than 4 hours. The PMT of the acetone distillate removed overhead was less than that of the sidedraw.

EXAMPLE 5

Example 4 was repeated except that the crude acetone vapour was fed to the column at 1120 ml h$^{-1}$, a 5% w/w aqueous sodium hydroxide solution was added to the column at a rate of 50 ml h$^{-1}$, the reboiler was maintained at 95° C. and the reflux to sidedraw ratio was 6.2:1. The liquid acetone sidedraw met BS 509:1971 and in particular had a PMT greater than 4 hours. The PMT of the acetone distillate removed overhead was less than that of the sidedraw.

We claim:

1. A process for the recovery of pure acetone from a crude acetone fraction removed overhead as a vapour from a first column separating phenol and higher-boiling compounds as a bottom fraction from the cumene hydroperoxide cleavage reaction product which process comprises partially condensing the crude acetone fraction, returning the condensed portion of the crude acetone fraction to the first column as reflux, feeding the remaining portion of the crude acetone fraction whilst still in the vapour phase to an intermediate point in a second distillation column to which there is also continuously fed at a point above the acetone feedpoint a dilute aqueous solution of an alkaline material, removing from the base of the second column a residue fraction comprising compounds boiling above acetone, removing from a point in the second column intermediate between the alkaline material feed point and the top of the column as a liquid sidedraw fraction pure acetone having a permanganate time greater than 4 hours, and removing from the top of the second column as a vapour fraction acetone having a permanganate time less than that of the sidedraw fraction, condensing the acetone vapour fraction and returning to the second column at a point above the liquid acetone sidedraw removal point a portion of the condensate as reflux.

2. A process according to claim 1 wherein the alkaline material is an alkali or alkaline earth metal oxide, hydroxide or phenate.

3. A process according to claim 2 wherein the alkaline material is sodium hydroxide.

4. A process according to claims 1, 2 or 3 wherein the rate at which the alkaline material is fed to the second column is such that the concentration of the alkaline material in the residue fraction removed from the base of the column is in the range 0.01 to 5.0% w/w.

5. A process according to claim 1, 2 or 3 wherein the rate is such that the concentration of alkaline material in the residue fraction removed from the base of the column is in the range 0.2 to 0.4% w/w.

6. A process according to claims 1, 2 or 3 wherein the second column is operated at a reduced pressure in the range 0.3 to 0.8 bar absolute at the top of the column.

7. A process according to claim 1 wherein the second column is provided with a reboiler.

8. A process according to claim 7 wherein at a pressure at the top of the column of 0.6 bar the reboiler is maintained at a temperature in the range 80° to 120° C.

9. A process according to claims 1, 2 or 3 wherein that part of the condensed acetone vapour fraction removed from the top of the second column not returned to the column as reflux is recycled to another part of the phenol from cumene process.

10. A process according to claims 1, 2 or 3 wherein the reflux to sidedraw ratio in the second column is in the range 4:1 to 25:1.

* * * * *